US007547686B2

(12) United States Patent
Pettit et al.

(10) Patent No.: US 7,547,686 B2
(45) Date of Patent: Jun. 16, 2009

(54) COMBRETASTATIN A-3 PRODRUG

(75) Inventors: George R. Pettit, Paradise Valley, AZ (US); Mathew D. Minardi, Chandler, AZ (US)

(73) Assignee: Arizona Board of Regents, a body corporate of the State of Arizona, Acting for and on Behalf of the Arizona State University, Scottsdale, AZ (US)

( * ) Notice: Subject to any disclaimer, the term of this patent is extended or adjusted under 35 U.S.C. 154(b) by 0 days.

(21) Appl. No.: 10/398,543

(22) PCT Filed: Jun. 17, 2002

(86) PCT No.: PCT/US02/19085

§ 371 (c)(1),
(2), (4) Date: Apr. 7, 2003

(87) PCT Pub. No.: WO02/102766

PCT Pub. Date: Dec. 27, 2002

(65) Prior Publication Data

US 2004/0029838 A1 Feb. 12, 2004

Related U.S. Application Data

(60) Provisional application No. 60/298,606, filed on Jun. 15, 2001.

(51) Int. Cl.
*A61K 31/66* (2006.01)
*C07F 9/02* (2006.01)

(52) U.S. Cl. ........................................ 514/107; 558/156

(58) Field of Classification Search ................. 558/156; 514/107

See application file for complete search history.

(56) References Cited

U.S. PATENT DOCUMENTS 5,561,122 A * 10/1996 Pettit .......................... 514/130
5,569,786 A * 10/1996 Pettit et al. .................. 568/646

FOREIGN PATENT DOCUMENTS

EP 0 276 051 7/1988
WO WO 99/35150 7/1999

OTHER PUBLICATIONS

Pettit et al., Canadian Journal of Chemistry, vol. 65, pp. 2390-2396, (1987).*

Pettit et al., Anti-Cancer Drug Design, vol. 13, pp. 981-993, (1998).*

Grosios et al., British Journal of Cancer, vol. 81, No. 8, pp. 1318-1327, (1999).*

Pettit et al., Anti-Cancer Drug Design, vol. 15, pp. 203-216, (2000).*

Parkins et al., British Journal of Cancer, vol. 83, No. 6, pp. 811-816, (2000).*

Pettit et al., Anti-Cancer Drug Design (1998), 13, 183-191.*

Pettit et al., Anticancer Drug Des. (1995), 10(4), 299-309 (abstract only).*

Pettit et al., "Antineoplastic agents 463. Synthesis of combretastatin A-3 diphosphate prodrugs," Anti-Cancer Drug Design, vol. 15, pp. 397-403, (2000).

Greenwald et al., "Drug Delivery Systems: Water Soluble Taxol 2'-Poly(ethylene glycol) Ester Prodrugs—Design and in Vivo Effectiveness", *J. Med. Chem.*, 39:424-431 (1996).

Lazar et al., "A Selective Removal of Benzyl Protecting Groups in Arylphosphate Esters with Bromotrimethylsilane", *Synthetic Communications*, 22(6):923-931 (1992).

Mamber et al., "Tubulin Polymerization by Paclitaxel (Taxol) Phosphate Prodrugs after Metabolic Activation with Alkaline Phosphatase", *The Journal of Pharmacology and Experimental Therapeutics*, 274(2):877-883 (1995).

Pettit et al., "Antineoplastic agents 460. Synthesis of Combretastatin A-2 Prodrugs", *Anti-Cancer Drug Design*, 16:185-193 (2001).

Ueda et al., "Novel Water Soluble Phosphate Prodrugs of Taxol® Possessing In Vivo Antitumor Activity", *Bioorganic & Medicinal Chemistry Letters*, 3(8):1761-1766 (1993).

Vyas et al., "Synthesis and Antitumor Evaluation of Water Soluble Taxol Phosphates", *Bioorganic & Medicinal Chemistry Letters*, 3(6):1357-1360 (1993).

Office Action dated May 9, 2007 for corresponding EP application No. 02 746 550.9 (3 sheets).

Office Action dated Aug. 18, 2008 for corresponding EP application No. 02 746 550.9 (5 sheets).

* cited by examiner

*Primary Examiner*—Rebecca L Anderson
(74) *Attorney, Agent, or Firm*—McAndrews Held & Malloy Ltd.

(57) ABSTRACT

A new and more efficient synthesis of combretastatin A-3 (2*a*) was completed (8.4% overall yield) starting from methyl gallate and isovanillin with aldehyde 5 and phosphonium salt 8 as key intermediates. Conversion of combretastatin A-3 (2*a*) to a series of diphosphate prodrugs (lO*a*-lO*l*) containing selected anions was achieved. Both the diphosphate sodium (lO*a*) and potassium salts (lO*c*) displayed aqueous solubility in excess of 220 mg/ml at room temperature and good cancer cell line inhibitory activity.

6 Claims, No Drawings

COMBRETASTATIN A-3 PRODRUG

This application is the U.S. national stage of PCT/US02/19085 filed on Jun. 17, 2002, which claims the priority of U.S. Provisional Application Ser. No. 60/298,606 filed on Jun. 15, 2001, which are incorporated herein by reference.

This Research was funded in part by Outstanding Investigator Grant CA-44344-05-12 awarded by the Division of Cancer Treatment, National Cancer Institute, DHHS. The United States Government may have certain rights to this invention.

INTRODUCTION

The present invention relates generally to the field of antineoplastic agents and more particularly to novel and unexpectedly beneficial methods of synthesizing combretastatin A-3 and thereafter converting combretastatin A-3 into a series of diphosphate prodrugs containing an anion selected from the group consisting of sodium, lithium, potassium, rubidium, calcium, zinc, manganese and magnesium and an amine selected from the group consisting of quinine, quinidine, morpholine and nicitinamide.

BACKGROUND

The preclinical (Pettit et al., 1995, *Anti-Cancer Drug Design,* 10, 299; 1995, *Journal of Medicinal Chemistry,* 38, 1666; 1998, *Anti-Cancer Drug Design,* 13, 183; Groslow et al., 1997, *British Journal of Cancer,* 81, 1318; Chaplin et al., 1999, *Anticancer Research,* 19, 189; Dark et al., 1997, *Cancer Research,* 57, 1829; Zhao et al., 1999, *European Journal of Nuclear Medicine,* 26, 236; Li et al., 1998, *Int. J. Radiation Oncology Biol. Phys.,* 42, 899; Horsman et al., 1998, *Int. J. Radiation Oncology Biol. Phys.,* 42, 895; Roberson et al., 1998, *Mycol. Res.,* 102, 378) and clinical development (currently Phase I human cancer clinical trials), (Remick et al., 1999, *Molecular Targets and Cancer Therapeutics Discover, Development, and Clinical Validation*. Proceedings of the AACR-NCI-EORTC International Congress, Washington, D.C. #16, p. 4; Rustin et al., 1999, *Molecular Targets and Cancer Therapeutics Discovery, Development, and Clinical Validation*. Proceedings of the AACR-NCI-EORTC International Congress, Washington, D.C. #14, p. 4) of the powerful cancer antiangiogenesis (Pluda, 1997, *Seminars in Oncology,* 24, 203) natural product combretastatin A-4 (1a) and its sodium phosphate prodrug (1b) has stimulated a variety of new research endeavors directed at structural modifications. Illustrative are a new synthesis of the (Z)- and (E)-combretastatin A-4 (Lawrence et al., 1999, *Synthesis,* 9, 1656), synthesis of benzofuran (Banwell et al., 1999, *Aust, J. Chem.* 52, 767), diarylindole (Medarde et al., 1999, *Bioorganic & Medicinal Chemistry Letters,* 9, 2303), heterocombretastatin (Rey et al., 1999, *Bioorganic & Medicinal Chemistry Letters,* 9, 2711; Medarde et al., 1998, *European journal of Medicinal Chemistry,* 33, 71; Ohsumi et al., 1998, *Journal of Medicinal Chemistry,* 41, 3022) and combretadioxolane (Shirai et al., 1998, *Bioorganic & Medicinal Chemistry Letters,* 8, 1997) analogs. One of the most advanced (preclinical development) structural modifications of combretastatin A-4 is the L-serine amide of the amino replacement for the phenol group of stilbene 1a known as AC-7700 (Nihei et al., 1999, *Japanese Journal of Cancer Research,* 90, 1016).

The present invention is predicated upon a continued pursuit of further SAR studies of the most active constituents that earlier isolated from the Southern African bushwillow *Combretum caffrum* (Pettit and Rhodes, 1998, *Anti-Cancer Drug Design,* 13, 183), with a focus on synthetic conversions to phosphate salt prodrugs suitable for preclinical development. The present study was directed at obtaining useful diphosphate prodrugs based on combretastatin A-3 (2a, Pettit et al., 1987, *Canadian Journal of Chemistry* 65, 2390). The rational for targeting these new phosphate prodrugs was based on anticipated increases in aqueous solubility and transport in vivo to metastatic tumors, followed by rapid enzymematic cleavage of the phosphate ester bond by the greatly increased levels of phosphatases in the cancer tissue. Such exceptionally useful properties had been previously observed in the combretastatin A-4 phosphate prodrug. (See: Nabha et al. 2000, *Anti-Cancer Drugs,* 11, 385)

SUMMARY OF THE INVENTION

A new and more efficient synthesis of combretastatin A-3 (2a) was completed (8.4% overall yield) starting from methyl gallate and isovanillin with aldehyde 5 and phosphonium salt 8 as key intermediates. Conversion of combretastatin A-3 (2a) to a series of diphosphate prodrugs (10a-10l) containing selected anions was achieved. Both the diphosphate sodium (10a) and potassium salts (10c) displayed aqueous solubility in excess of 220 mg/ml at room temperature and good cancer cell line inhibitory activity.

Accordingly a principal object of the present invention is the development of an economically viable synthesis of combretastatin A-3 employing methyl gallate and isovanillin with aldehyde and phosphorous salt as key intermediates and thereafter converting combretastatin A-3 into a series of diphosphate prodrugs.

Another object of the present invention is the development and utilization of a new and improved antineoplastic agent containing selected diphosphate prodrugs of combretastatin A-3 as their essential active ingredient.

This and still further objects as shall hereinafter appear are readily fulfilled by the present invention in a remarkably unexpected matter as will be readily discerned from the following detailed description of exemplary embodiments thereof.

DETAILED DESCRIPTION OF PREFERRED EMBODIMENTS

All solvents were anhydrous and other reagents were from the sources summarized in the preceding contribution (Pettit et al., 2000). Gravity column chromatography was performed using silica gel (70-230 mesh) from VWR Scientific. All melting points were determined with an Electrochemical digital melting point apparatus, model IA 9200, and are uncorrected. NMR spectra were recorded employing Varian Gemini 300 or Varian Unity 400 instruments. Chemical shifts are reported in ppm downfield from tetramethylsilane as internal standard. High resolution FAB mass spectra were obtained with a Kratos MS-50 unit (Midwest Center for Mass Spectrometry, University of Nebraska-Lincoln). Elemental analyses were obtained from Galbraith Laboratories, Inc., Knoxville, Tenn. Abbreviations: LAH, lithium aluminum hydride; PCC, pyridinium chlorochromate; TBDMS-Cl, t-butylchlorodimethylsilane; TBDMS, t-butyldimethylsilane; DIPEA, diisopropylethyl amine; DMF, N,N-dimethylformamide; THF, tetrahydrofuran; DCM, dichloromethane; TLC, thin layer chromatography.

Methyl-3-O-tert-butyldimethylsilyloxy-4,5-dimethoxy-benzoate (3)

To a flame-dried 5L RB flask was added DMF (1 L), TBDMS-Cl (72 g, 0.476 mol) and DIPEA (80 ml, 0.46 mol). The solution was stirred (magnetically) for 10 minutes, methyl gallate (80 g, 0.43 mmol) was added, stirring continued (under argon) for 2 hours and NaH (60%, 56 g, 1.4 mol) was added (over 30 minutes while the solution turned green). Iodomethane (90 ml, 1.44 mol) was added and the solution turned red while stirring was continued for 4 hours. The reaction was terminated by the addition of water (500 ml) and extracted with hexane (4×1 L). The solvent was removed in vacuo and the residue purified by column chromatography (5:95 ethyl acetate-hexane as eluent) to afford 54.7 g of a clear oil (2, 39% yield); 1H NMR (300 MHz, CDCl3) δ 0.19 (s, Si(CH3)2), 1.00 (s, C(CH3)3), 3.83 (s, OCH3), 3.88 (s, OCH3), 3.89 (s, OCH3), 7.20 (d, ArH, J=1.8 Hz), 7.25 (d, ArH, J=1.8 Hz); 13C NMR (75 MHz, CDCl3) δ −4.88, 18.08 , 25.46, 51.84, 55.82, 60.15, 106.60, 115.68, 124.95, 144.49, 148.49, 153.27, 166.37. IR 2955, 2860, 1718, 1585, 1498, 14.21, 1350 cm-1. Anal. calcd for Cl6H26O5Si: C, 58.87; H, 8.03; O, 24.50. Found: C, 58.95; H, 8.10.

3-O-Tert-butyldimethylsilyloxy)-4,5-dimethoxy-benzyl Alcohol (4)

THF (200 ml) and LAH (3.6 g, 97 mmol) were added to a flame-dried 1 L RB flask. The solution was stirred 10 minutes (under argon) and methyl ester 3 (29 g, 89 mmol, in 20 ml THF) was added (dropwise) over 30 minutes. After 3 hours the reaction was terminated by the addition (dropwise) of 5 ml of water followed by brine (300 ml). The solution was filtered through a 5 cm bed of silica gel and the chromatographic substrate was extracted with ethyl acetate. Solvent was removed in vacuo to afford 26 g of a clear oil (4, 98% yield, cf Pettit and Singh, 1987, *Canadian Journal of Chemistry,* 65, 2390); 1H NMR (300 MHz, CDCl3) δ 0.18 (s, Si(CH3)2), 1.01 (s, C(CH3)3), 3.78 (s, OCH3), 3.86 (s, OCH3), 4.58 (s, ArCH2), 6.50 (s, ArH), 6.59 (s, ArH).

4,5-Dimethoxy-3-O-tert-butyldimethylsilyloxy-benzaldehyde (5)

To a stirred solution of PCC (3 g, 14 mmol) and sodium acetate (1.2 g, 14 mmol) in DCM (100 ml) was added (dropwise) benzyl alcohol 4 (3.8 g, 13 mmol) in DCM (20 ml). The reaction mixture was stirred 16 hours at room temperature, passed through a 5 cm layer of silica gel and the solvent removed in vacuo. The residue was purified by column chromatography employing 1:9 ethyl acetate-hexane as eluent to afford aldehyde 5, 3.4 g, 98% yield (cf. Singh and Pettit, 1989,) as a colorless oil; 1H NMR (300 MHz, CDCl3) δ 0.20 (s, Si(CH3)2), 1.02 (s, C(CH3)3), 3.87 (s, OCH3), 3.92 (s, OCH3), 7.02 (d, ArH, J=1.8 Hz), 7.11 (d, ArH, J=1.8 Hz), 9.82 (s, C(O)H).

3-O-Tert-butyldiphenylsilyloxy-4-methoxy-benzaldehyde (6)

To a 1 L round-bottom flask was added DMF (400 ml), isovanillin (50 g, 329 mmol), TBDPS-Cl (100 g, 365 mmol, 1.1 eq) and imidazole (45 g, 661 mmol, 2 eq). The reaction mixture was stirred for 16 hours under argon. The reaction was terminated by the addition of water (500 ml), followed by extraction with hexane. The solvent was removed in vacuo and the residue purified by column chromatography (9:1 hexane-ethyl acetate as eluant) to afford 117 g (6, in 92% yield) as a colorless solid, m.p. 96-97° C. (from hexane); IR 2858, 1687, 1595, 1510, 1429, 1282, 1116, 910 cm-1; 1H NMR (300 MHz, CDCl3) δ 1.12 (s, C(CH3)3), 3.55 (s, OCH3), 6.79 (d, ArH, J=8.1 Hz), 7.25 (d, ArH, J=1.8 Hz), 73.9 (m, 7 ArH), 7.68 (m, 4 ArH), 9.66 (s C(O)H); 13C NMR 19.76, 26.60, 55.10, 111.17, 120.08, 125.57, 127.51, 129.73, 129.86, 133.05, 135.25; 145.42, 155.98, 190.73. HRMS (M+) 391.1740; Anal. calcd for C24H26O3S: C, 73.81; H, 6.71. Found: C, 73.94; H, 6.74.

3-O-Tert-butyldiphenylsilyoxly-4-methoxy-benzyl Alcohol (7)

A solution of aldehyde 6 (111.5 g, 285 mmol) in ethanol (700 ml) was stirred 10 minutes and NaBH4 (13 g, 343 mmol, 1.2 eq) was added (portionwise) to the cloudy mixture over 30 minutes. After stirring for 3 hours, solid NaHCO3 was added until effervescence stopped. The solution phase was filtered and the solvent removed in vacuo to afford alcohol 7 (112 g) in 99% yield as a colorless solid: mp 111-113° C.; 1H NMR (300 MHz, CDCl3) δ 1.11 (s, C(CH3)3), 3.51 (s, OCH3), 4.39 (s, CH2), 7.16 (d, ArH, J=8.1 Hz), 7.10 (d, ArH J=1.5 Hz), 6.82 (dd, ArH J=8.1, 1.5 Hz), 7.33 (m, 6 ArH), 7.68 (m, 4 ArH); 13C NMR 19.74, 26.65, 55.28, 64.88, 112.18, 119.41, 120.31, 127.43, 129.53, 133.38, 133.62, 134.76, 135.33, 145.03, 150.06. HRMS (M+Li)+399.1959; Anal. calcd for C24H28O3Si: C, 73.43; H, 7.19. Found: C, 73.20; H, 7.13.

3-O-Tert-butyldiphenylsilyloxy-4-methoxybenzyltriphenylphosphonium Bromide (8)

A solution benzyl alcohol 7 (84 g, 214 mmol) in DCM (400 ml) was added PBr3 (10 ml, 106 mmol, 0.5 eq). The reaction mixture was stirred 16 hours and the reaction was terminated by the addition of 10% NaHCO followed by extraction with DCM. The solvent was removed (in vacuo) and to the resulting benzyl bromide dissolved in toluene (500 ml) PPh3 (62 g, 236 mmol, 1.1 eq) was added. The mixture was heated at reflux for 1 hour, then stirred for 15 hours. The precipitate was collected and triturated with ether to afford phosphonium bromide 8 (132 g) in 86% yield. Recrystallization from methanol afforded a colorless solid, mp 150-151° C.; 1H NMR (300 MHz, CD3OD) 1.00 (s, 9H), 3.51 (s, 3H), 4.69 (d, Jpch2, 7.4 Hz), 6.34 (dt, J=2.4, 8.2 Hz), 6.59 (d, J=8.1 Hz), 6.65 (t, J=2.4 Hz); 13C NMR (75 MHz, CD3OD) δ 20.47, 27.07, 55.60, 102.20, 113.15, 118.48, 119.60, 123.43, 126.56, 126.85, 128.17, 128.74, 131.07, 131.12, 131.29, 133.91, 135.10, 135.23, 136.17, 136.55, 146.55, 152.76. Anal. calcd for C42H42BrO2PSi: C, 70.28; H, 5.90. Found: C,69.83; H. 6.05.

3,5-Di-tertbutyldimethylsiloxy-combretastatin A-3 (9)

A mixture composed of THF (250 ml in a 1 L 3 neck flask) and phosphonium bromide 8 (38 g, 53 mmol) was stirred and cooled to −78° C., at which time 2.5 M n-butyllithium (21 ml, 53 mmol) was added. Stirring was continued 2 hours and benzaldehyde 5 (13 g, 44 mmol dissolved in 50 ml of THF) was added (dropwise over 30 minutes). The reaction was allowed to warm to room temperature and stirred an additional 2 hours. The reaction was completed by the addition of water (100 ml), followed by extraction with ethyl acetate and removal of the organic solvent (in vacuo). Separation of the residue by column chromatography (3:97 ethyl acetate-hexane as eluent) afforded 9 (3.3 g, 29%); b.p. dec 290° C. (0.1 mm); 1H NMR (300 MHZ, CDCl3), δ 0.11 (s, Si(CH3)2), 0.97 (s, C(CH3)3), 1.07 C(CH3)3), 3.43 (s, OCH3), 3.63 (s, OCH3), 3.76 (s, OCH3), 6.27 (s, 2 vinyl H), 6.38 (d, ArH, J=2.1 Hz), 6.43 (d, ArH, J=2.1 Hz), 6.56 (d, ArH, J=8.1 Hz), 6.72 (d, ArH, J=2.1 Hz), 6.77 (dd, ArH, J=2.1, 8.4 Hz), 7.33 (m, 6 ArH), 7.65 (m, 4 ArH); 13C NMR −5.09, 17.87, 19.37, 22.16, 25.27, 26.27, 28.58, 54.86, 55.46, 59.96, 102.60, 111.71, 112.05, 117.09, 120.02, 126.00, 126.91, 127.06, 129.00, 129.14, 129.78, 132.71, 133.30, 134.80, 134.99, 139.49, 144.75, 148.96, 149.85, 153.26.

Combretastatin A-3 (2a)

A solution prepared from THF (50 ml), disilyl ether 9 (3.3 g, 5 mmol) and 1 M TBAF (11 ml, 11 mol) was stirred for 3 hours. Termination of the reaction was performed by the addition of 6N HCl (40 ml). Ethyl acetate extract of the mixture was dried over sodium sulfate and the solvent removed in vacuo. Separation by column chromatography using 1:1 hexane-ethyl acetate as eluent afforded combretastatin A-3 (2a, 1.5 g, 99%) as an oil (Lit., oil, Pettit and Singh, 1987); b.p. dec 243° C. (0.1 mm); 1H NMR (300 MHZ, CDCl3), δ 3.68 (s, OCH3), 3.88 (s, OCH3), 3.90 (s, OCH3), 5.50 (s, ArOH), 5.66 (s, ArOH), 6.38 (d, vinyl H, J=12 Hz), 6.46 (d, vinyl H, J=12 Hz), 6.44 (s, ArH), 6.54 (d, ArH, J=1.8 Hz), 6.74 (d, ArH, J=8.4 Hz), 6.80 (dd, ArH, J=8.4, 1.8 Hz), 6.91 (d, ArH, J=1.8 Hz).

3,3'-O-Bis(benzyl)phosphoryl-3,4,4'-trimethoxy-(Z)-stilbene (2b)

Diisopropylethyl amine (6.6 ml, 38 mmol), dimethylaminopyridine (226 mg, 1.9 mmol) and following 1 minute dibenzylphosphite (6 ml, 27 mmol) was added (dropwise over 5 minutes) to a solution prepared (consecutively) from acetonitrile (30 ml) bis-phenol 2a (2.8 g, 9.3 mmol) and CCl4 (9 ml, 93 mmol), cooled to −10° C. and stirred 10 minutes. The reaction mixture was stirred 3 hours at −10° C. and treated with $KH_2PO_4$ (50 ml, 0.5 m), stirred 10 minutes and then extracted with ethyl acetate. Removal (in vacuo) of solvent and separation by column chromatography (1:1 hexane-ethyl acetate elution) gave 5.8 g (2b, 76% yield) as a colorless oil; $^1$H NMR (300 MHZ, $CDCl_3$) δ 3.59 (s, $OCH_3$), 3.72 (s, $OCH_3$), 3.80 (s, $OCH_3$), 5.10 (s, $2CH_2$), 5.13 (s, $2CH_2$), 6.33 (d, vinyl H, J=12 Hz), 6.40 (d, vinyl H, J=12 Hz), 6.63 (s, ArH), 6.73 (s, ArH), 6.76 (s, ArH), 7.04 (d, ArH, J=8.7 Hz), 7.09 (s, ArH); $^{13}$C NMR (100 MHZ, $CDC_{13}$) δ 153.16, 149.76, 149.72, 143.86, 143.80, 139.45, 139.42, 139.39, 139.35, 135.63, 135.56, 135.48, 132.47, 129.74, 129.72, 128.99, 128.59, 128.43, 128.41, 128.37, 127.87, 127.86, 127.77, 126.34, 126.36, 122.17, 122.14, 114.39, 114.36, 112.31, 109.42, 11.21, 61.12, 55.91, 55.90; 31P NMR(162 MHZ, $CDCl_3$) −7.82, −8.09; Anal. calcd for $C_{45}H_{44}O_{11}P_2$: C, 65.69; H, 5.39. Found: C, 65.70; H, 5.56.

General Procedure for Synthesis of Combretastatin A-3 Phosphate Prodrugs

Sodium combretastatin A-3 3,3'-O-phosphate (10a)

Trimethylbromosilane (0.6 ml, 4.5 mmol) was added to a solution of bisphosphate 2b (0.9 g, 1.1 mmol) in DCM (10 ml). After stirring 30 minutes under argon, the reaction was completed by the addition of methanol (20 ml). Following removal (in vacuo) of solvent the resulting oil (2c) was dissolved in water (10 ml) and washed with hexane (15 ml). Water was removed in vacuo and the phosphoric acid residue was dissolved in ethanol (10 ml). Sodium methoxide (0.25 g, 1.1 mmol) was added and the mixture stirred for 30 minutes. The solvent was removed in vacuo and the colorless solid was recrystallized from water-acetone to afford bis-sodium phosphate 10a (1.6 g) as a colorless solid.

Antimicrobial susceptibility testing. Compounds were screened against the bacteria *Stenotrophomonas maltophilia, Micrococcus luteus, Staphylococcus aureus, Escherichia coli, Enterobacter cloacae, Enterococcus faecalis, Streptococcus pneumoniae, Neisseria gonorrhoeae*, and the fungi *Candida albicans* and *Cryptococcus neoformans, according to established disk susceptibility testing protocols (National Committee for Clinical Laboratory Standards* 1997. Performance standards for antimicrobial disk susceptibility tests-sixth edition: Approved Standard M2-A6, NCCLS, Wayne, Pa.)

Results and Discussion

The original synthesis of combretastatin A-3 (Pettit and Singh, 1987, *Canadian Journal of Chemistry,* 65, 2390) was initially improved by reversing the reactive functional groups in the Wittig olefin synthesis. Subsequently, we were able to make further refinements by selectively silylating methyl gallate with tert-butylchlorodimethylsilane followed by methylation with methyl iodide in N,N-dimethylformamide to yield dimethyl ether 3. Benzoate 3 was next reduced (3→4) using lithium aluminum hydride in tetrahydrofuran and the product oxidized to aldehyde 5 with pyridinium chlorochromate in dichloromethane. The B ring unit was synthesized by first protecting isovanillin using tert-butylchlorodiphenyl-silane. The resulting silylether-protected isovanillin (6) was reduced using sodium borohydride in ethanol to benzyl alcohol 7. Treatment of alcohol 7 with phosphorous tribromide, followed by triphenylphosphine led to phosphonium salt 8. The Wittig reaction employing aldehyde 5 and the yield resulting from reaction of phosphonium salt 8 and n-butyl lithium in tetrahydrofuran at −78° C. afforded stilbene 9. Deprotection using tetrabutylammonium fluoride provided combretastatin A-3 in good overall yield (8.4%). The choice of two different silylether protecting groups for rings A and B arose from the need to employ a ring B protecting group that was found to better survive the Wittig reaction step and provide a future advantage in allowing selective removal of the ring A silylether group.

Phosphorylation (Silverberg et al., 1996, *Tetrahedron Letters,* 37, 771; Pettit and Rhodes, 1998, *Anti-Cancer Drug Design,* 13, 981) of combretastatin A-3 with dibenzyl phosphite provided phosphate 2b. Debenzylation of phosphate ester 2b was readily achieved using bromotrimethylsilane (Lazar and Guillaumet, 1992; Pettit et al., 2000). Use of the silyl bromide in place of the iodide (Pettit and Rhodes, 1998) was found (Pettit et al., 2000) to decrease conversion to the (E) isomer. Reaction of the resulting phosphoric acid with the respective base led to phosphate salts 10a-l.

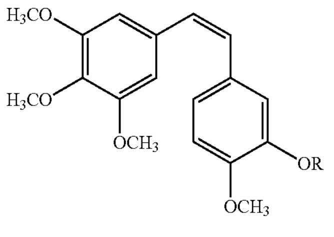

1a R = H Combretastatin A-4
1b R = $PO_3Na_2$ Combretastatin A-4 Prodrug

-continued

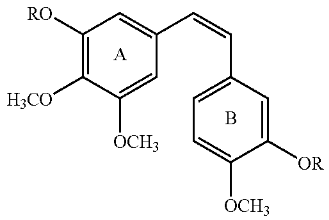

2a, R = H, Combretastatin A-3
2b, R = $PO(OBn)_2$
2c, R = $PO_3H_2$

Scheme 1[a]

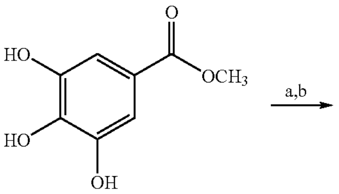

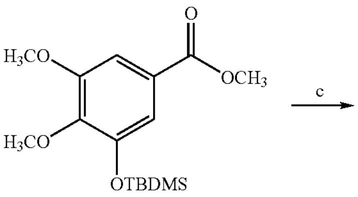

3

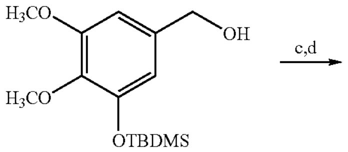

4

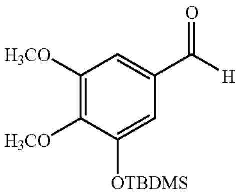

5

[a]Reagents and Conditions: (a) DIFEA, TBDMS—Cl, DMF; (b) NAH, $CH_3I$, DMF; (c) LAH, THF; (d) PCC, sodium acetate, DCM Scheme 2[a]

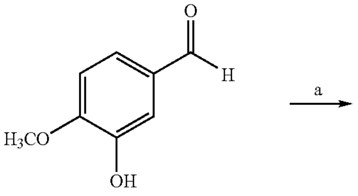

-continued

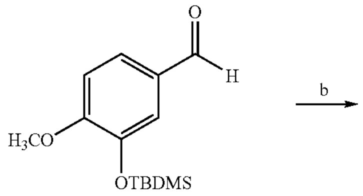

6

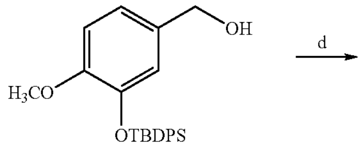

7

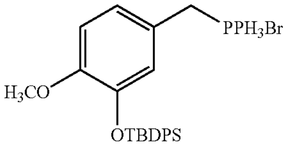

8

[a]Reagents and Conditions: (a) imidazole, TBDPS—Cl, DMF; (b) $NABH_4$, ethanol; (c) $PBr_3$, $CH_2Cl_2$; (d) $PPh_3$, $CH_2Cl_2$.

Scheme 3[a]

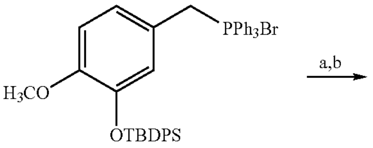

8

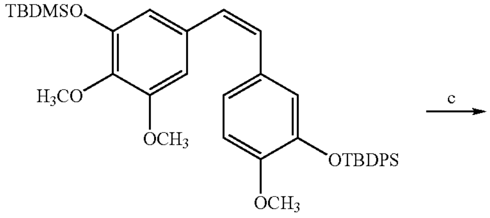

9

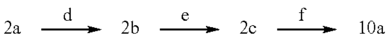

[a]Reagents and Conditions: (a) n-BuLi, THF, -78° C.; (b) 5, in 20 mL THF; (c) 1M TBAF; (d) $CCl_4$, DIPEA, DMAP, Dibenzyl phosphite, -10° C., ACN; (e) TMSBr, $CH_2Cl_2$; (f) $NaOCH_3$, ethanol.

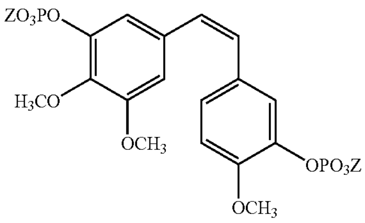

-continued

10a, Z = $Na^+$
b, Z = $Li^+$
c, Z = $K^+$
d, Z = $Rb^+$
e, Z = $Ca^{2+}$
f, Z = $Zn^{2+}$
g, Z = $Mg^{2+}$
h, Z = $Mg^{2+}$
i, Z = quinine
j, Z = quinidine
k, Z = morpholine
l, Z = nicotinamide

TABLE 1

Combretastatin A-3 Metal and Ammonium Diphosphate prodrugs.

| Compound | Purification Method | Mp. (° C.) | $^1$H NMR (300 MHz, δ)/IR Data (cm$^{-1}$) |
|---|---|---|---|
| 10a | A | 167-168 | $D_2O$ 3.47 (s, $OCH_3$), 3.72 (s, $OCH_3$), 3.73 (s, $OCH_3$), 6.43 (d, vinyl H, J=12 Hz), 6.50 (d, vinyl H, J=12 Hz), 6.57 (s, ArH), 6.84 (d, ArH, J=8.4 Hz), 6.93 (d, ArH, J=8.4 Hz), 6.92 (s, ArH), 7.19 (s, ArH) |
| 10b | A | dec 226-229 | $D_2O$ 3.45 (s, $OCH_3$), 3.71 (s, $OCH_3$), 3.72 (s, $OCH_3$), 6.41 (d, vinyl H, J=12 Hz), 6.52 (d, vinyl H, J=12 Hz), 6.54 (s, ArH), 6.81 (d, ArH, J=8.4 Hz), 6.90 (d, ArH, J=8.4 Hz), 6.94 (s, ArH), 7.21 (s, ArH) |
| 10c | A | 155-157 | $D_2O$ 3.50 (s, $OCH_3$), 3.74 (s, 2 $OCH_3$), 6.42 (d, vinyl H, J=12 Hz), 6.50 (d, vinyl H, J=12 Hz), 6.58 (s, ArH), 6.83 (d, ArH, J=8.7 Hz), 6.92 (d, ArH, J=8.7 Hz), 6.91 (s, ArH), 7.18 (s, ArH) |
| 10d | B | dec 215-281 | $D_2O$ 3.70 (s, $OCH_3$), 3.81 (s, $OCH_3$), 3.83 (s, $OCH_3$), 6.42 (d, vinyl H, J=12 Hz), 6.48 (d, vinyl H, J=12 Hz), 6.63 (s, ArH), 6.93 (s, ArH), 6.94 (s, ArH), 7.00 (s, ArH), 7.34 (s, ArH) |
| 10e | C | dec 245-248 | 2941, 2841, 1585, 1510, 1423, 1278, 1203, 1111, 1057 |
| 10f | C | dec 320-325 | 2943, 1610, 1510, 1450, 1429, 1271, 1116, 1012 |
| 10g | A | dec 247-249 | 2945, 1624, 1510, 1406, 1280, 1192, 1111, 1053, 950 |
| 10h | A | dec 240-242 | $D_2O$ 3.47 (s, $OCH_3$), 3.72 (s, $OCH_3$), 3.73 (s, $OCH_3$), 6.43 (d, vinyl H, J=12 Hz), 6.50 (d, vinyl H, J=12 Hz), 6.57 (s, ArH), 6.84 (d, ArH, J=8.4 Hz), 6.93 (d, ArH, J=8.4 Hz), 6.92 (s, ArH), 7.19 (s, ArH) |

TABLE 1-continued

Combretastatin A-3 Metal and Ammonium Diphosphate prodrugs.

| Compound | Purification Method | Mp. (° C.) | $^1$H NMR (300 MHz, δ)/IR Data (cm$^{-1}$) |
|---|---|---|---|
| 10i | B | 164-165 | $CD_3OD$ 1.37 (t, 4H), 1.76 (bs, 4H), 2.03 (m, 12H), 2.63 (m, 8H) 3.11 (m, 8H), 3.43 (m, 10H), 3.58 (s, $OCH_3$), 3.61 (s, $OCH_3$), 3.75 (s, $OCH_3$), 3.93 (s, 4-$OCH_3$), 4.92 (s, 3H), 5.00 (s, 3H), 5.06 (s 3H), 5.67 (m, 4H), 6.17 (s, 4H), 6.21 (d, vinyl H, J=12 Hz), 6.27 (d, vinyl H, J=12 Hz), 6.47 (s, 1H), 6.73 (d, 1H, J=8.4 Hz), 6.78 (d, 1H, J=8.4 Hz), 7.30 (s, 4H), 7.32 (s, 4H), 7.40 (s, 4H), 7.71 (m, 6H), 7.86 (s, 2H), 7.89 (s, 2H), 8.63 (bs, 4H) |
| 10j | C | 140-142 | $CD_3OD$ 0.83 (t, J=7.2 Hz), 1.2 (bs), 1.56 (s), 1.76 (s), 2.13 (t, J=9.9 Hz), 2.36 (d, J=7.2 Hz), 2.49 (s), 2.82 (m), 2.97 (m), 3.17 (m), 3.4 (s), 3.51 (m), 3.58 (s), 3.61 (s), 3.66 (s, $OCH_3$), 3.70 (s, $OCH_3$), 3.72 (s, $OCH_3$), 3.90 (s), 4.71 (bs), 4.77 (s), 5.09 (s), 5.11 (s), 5.15 (s), 5.77 (bs), 6.05 (t, J=17.4 Hz), 6.05 (dd), 6.30 (d, J=12.6 Hz), 6.35 (d, J=12.6 Hz), 6.53 (s), 6.57 (s), 6.87 (s), 7.21 (s), 7.34 (s), 7.37 (s), 7.55 (d, J=3.9 Hz), 7.91 (d, J=9.3 Hz), 8.68 (d, J=3.9 Hz). |
| 10k | C | oil | $CD_3OD$ 3.13 (bs, —$CH_2OCH_2$—), 3.83 (s, $OCH_3$), 3.84 (s, $OCH_3$), 3.86 (s, $OCH_3$), 3.85 (bs, —$CH_2NCH_2$—), 6.83 (s, ArH), 6.89 (d, ArH, J=3 Hz), 6.94 (d, vinyl H, J=7.5 Hz), 7.10 (d, vinyl H, J=7.5 Hz), 7.03 (d, J=5.1 Hz), 7.46 (s, ArH), 7.84 (s, ArH). |
| 10l | C | oil | ($CD_3OD$) 3.64 (s, $OCH_3$), 3.74 (s, $OCH_3$), 3.78 (s, $OCH_3$), 6.35 (d, 1H, J=12 Hz), 6.41 (d, 1H, J=12 Hz), 6.58 (d, ArH, J=1.8 Hz), 6.86 (d, ArH, J=8.1 Hz), 6.91 (d, ArH, J=1.5 Hz), 6.94 (d, ArH, J=1.5 Hz), 7.28 (s, ArH), 7.70 (m, 4H), 8.45 (s, 2H), 8.48 (s, 2H), 8.76 (bs, 4H), 9.09 (bs, 4H) |

Purification Method:
A) recrystallized from water-acetone;
B) recrystallized from acetone-methanol;
C) tritrated with ether.
Note:
IR data taken only when H NMR not possible due to solubility or paramagnetism

TABLE II

Human Cancer Cell Line and Murine P388 Lymphocytic Leukemia cell line Inhibitory Activity of combretastatin A-3, A-4, and synthetic modifications.

| Cell Line ($GI_{50}$ mg/mL Stilbene | Leukemia P388 | Pancreas-a BXPC-3 | Breast and MCF-7 | CNS SF268 | Lung-NSC NCI-H460 | Colon KM20 L2 | Prostate DU-145 |
|---|---|---|---|---|---|---|---|
| 1a | 0.0003 | 0.39 | — | <0.001 | 0.0006 | 0.061 | 0.0008 |
| 1b | 0.0004 | — | — | 0.036 | 0.029 | 0.034 | — |
| 2a | 0.257 | 2.3 | 0.49 | 0.0083 | 0.19 | 1.2 | 0.0043 |
| 2b | 2.97 | >10 | 5.7 | 3.6 | 8.0 | >10 | 2.4 |
| 10a | 0.305 | 2.8 | 0.92 | 0.052 | 0.45 | 3.5 | 0.048 |
| 10b | 0.0426 | 3.0 | 0.032 | 0.023 | 0.42 | 3.7 | 0.024 |
| 10c | 0.0152 | 4.4 | 0.39 | 0.20 | 2.4 | 2.1 | 0.11 |
| 10d | 0.0145 | 2.8 | 0.19 | 0.032 | 0.37 | 3.5 | 0.032 |
| 10e | 3.15 | 1.1 | 0.048 | 0.025 | 0.22 | 1.9 | 0.028 |
| 10f | 0.0124 | >10 | 19.3 | >10 | >10 | 24.8 | 17.4 |

TABLE II-continued

Human Cancer Cell Line and Murine P388 Lymphocytic Leukemia cell line Inhibitory Activity of combretastatin A-3, A-4, and synthetic modifications.

| Cell Line ($GI_{50}$ mg/mL Stilbene | Leukemia P388 | Pancreas-a BXPC-3 | Breast and MCF-7 | CNS SF268 | Lung-NSC NCI-H460 | Colon KM20 L2 | Prostate DU-145 |
|---|---|---|---|---|---|---|---|
| 10g | <0.0100 | 1.8 | 0.055 | 0.025 | 0.28 | 2.3 | 0.032 |
| 10h | 0.0130 | 0.45 | 0.030 | 0.0051 | 0.23 | 0.36 | 0.0043 |
| 10i | 0.0321 | 4.3 | 0.36 | 0.052 | 0.72 | 3.9 | 0.042 |
| 10j | 0.0238 | 6.7 | 0.54 | 0.22 | 1.3 | 9.7 | 0.40 |
| 10k | <0.0100 | >1 | >1 | 0.64 | >1 | >1 | 0.58 |
| 10l | 0.0161 | 1.6 | 0.33 | 0.041 | 0.37 | 2.1 | 0.049 |

TABLE III

Solubility of combretastatin A-3 Diphosphate Salts (10a-1) in mg/mL at 25° C.

| Diphosphate | 10a | 10b | 10c | 10d | 10e | 10f | 10g | 10h | 10i | 10j | 10k | 10l |
|---|---|---|---|---|---|---|---|---|---|---|---|---|
| Solubility | >218 | >100 | >228 | >60 | 3 | <1 | <2 | 10 | <1 | <1 | >40 | 27 |

Most of the prodrug candidates (10a-l) retained potent tumor cell growth-inhibitory activity (Table II), but candidates 10a-d showed substantially better aqueous solubility than did 10e-j (Table III). Contemporaneous, comparative testing of the parent combretastatin A-3 (2a) with its disodium phosphate prodrug (10a) in the NCI 60-cell screen (Boyd, 1997,) yielded mean-panel GI50values (X10-8MISE) of 6.57 1.84 and 10.3 1.8, respectively. Compare correlation analyses (Boyd and Paull, 1995) confirmed that the mean-graph profiles of 2a and 10a were essentially indistinguishable.

The combretastatins are moderately antimicrobial (Pettit et al., 1995; Pettit et al., 1998; Pettit et al., 2000; Pettit and Lippert, 2000). Indeed, the majority of the natural combretastatins and their derivatives are antibacterial; however, (E)-combretastatin A-1 has antibacterial and antifungal activities (Pettit et al., 2000). In disk diffusion assays, combretastatin A-3 (2a) was selective for the pathogenic fungus Cryptococcus neoformans (MIC=50-100 μg/disk). The sodium phosphate prodrug (10a) of combretastatin A-3 (2a) was not active in these assays.

Dosages

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate., calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection. and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water; a dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies either phenstatin 3b and/or phenstatin prodrug 3d, and/or benzophenones 4a-f or any other compound described herein.

Composition "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 200 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient-in 50, 250 and 500 mg amounts by substituting 50 g, 250 g and 500 g of an active ingredient for the 200 g used above.

Composition "B"

Soft Gelatin Capsules

One-piece soft gelatin capsules for oral use, each containing 200 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

Composition "C"

Tablets

One thousand tablets, each containing 200 mg of an active ingredient, are prepared from the following types and amounts of ingredients:

| | | |
|---|---|---|
| Active ingredient, micronized | 200 | g |
| Lactose | 300 | g |
| Corn starch | 50 | g |
| Magnesium stearate | 4 | g |
| Light liquid petrolatum | 5 | g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing an active ingredient in 250 mg and 100 mg amounts by substituting 250 g and 100 g of an active ingredient for the 200 g used above.

Composition "D"

Oral Suspension

One liter of an aqueous suspension for oral use, containing in each teaspoonful (5 ml) dose, 50 mg of an active ingredient, is prepared from the following types and amounts of ingredients:

| | | |
|---|---|---|
| Active ingredient, micronized | 10 | g |
| Citric acid | 2 | g |
| Benzoic acid | 1 | g |
| Sucrose | 790 | g |
| Tragacanth | 5 | g |
| Lemon Oil | 2 | g |
| Deionized water, q.s. | 1000 | ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

Composition "E"

Parenteral Product

A sterile aqueous suspension for parenteral injection, containing 30 mg of an active ingredient in each milliliter for treating a neoplastic disease, is prepared from the following types and amounts of ingredients:

| | | |
|---|---|---|
| Active ingredient, micronized | 30 | g |
| POLYSORBATE 80 | 5 | g |
| Methylparaben | 2.5 | g |
| Propylparaben | 0.17 | g |
| Water for injection, q.s. | 1000 | ml. |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic. disease at a dose of 1 milliliter (1 ml) three times a day.

Composition "F"

Suppository, Rectal and Vaginal

One thousand suppositories, each weighing 2.5 g and containing 200 mg of an active ingredient are prepared from the following types and amounts of ingredients:

| | | |
|---|---|---|
| Active ingredient, micronized | 15 | g |
| Propylene glycol | 150 | g |
| Polyethylene glycol #4000, q.s. | 2,500 | g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

Composition "G"

Intranasal Suspension

One liter of a sterile aqueous suspension for intranasal instillation, containing 20 mg of an active ingredient in each milliliter, is prepared from the following types and amounts of ingredients:

| | | |
|---|---|---|
| Active ingredient, micronized | 15 | g |
| POLYSORBATE 80 | 5 | g |
| Methylparaben | 2.5 | g |
| Propylparaben | 0.17 | g |
| Deionized water, q.s. | 1000 | ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

Composition “I”

Oral Powder

One hundred grams of an active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

Composition “J”

Insufflation

One hundred grams of an active ingredient in bulk form is finely divided by means of an air micronizer.

The foregoing composition is useful for treating a neoplastic disease, by the inhalation of 300 mg one to four times a day.

From the foregoing, it becomes readily apparent that a new and useful antineoplastic factor and new and useful antinceoplastic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention.

The invention claimed is:

1. A method for preparing a Combretastatin A-3 diphosphate prodrug having the following structure:

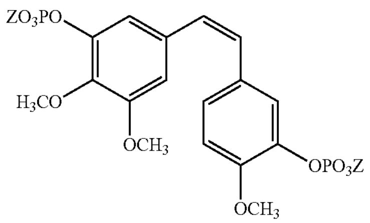

wherein Z is Na, said method comprising performing the reactions as set forth below in the following reaction scheme:

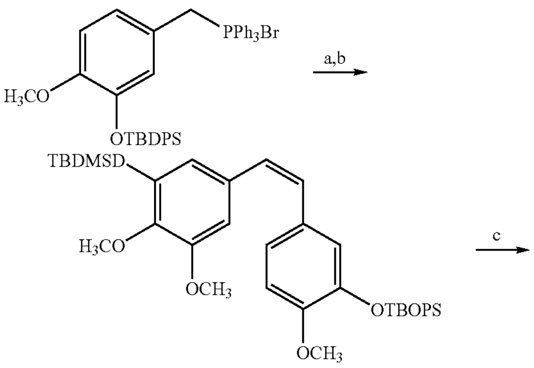

-continued

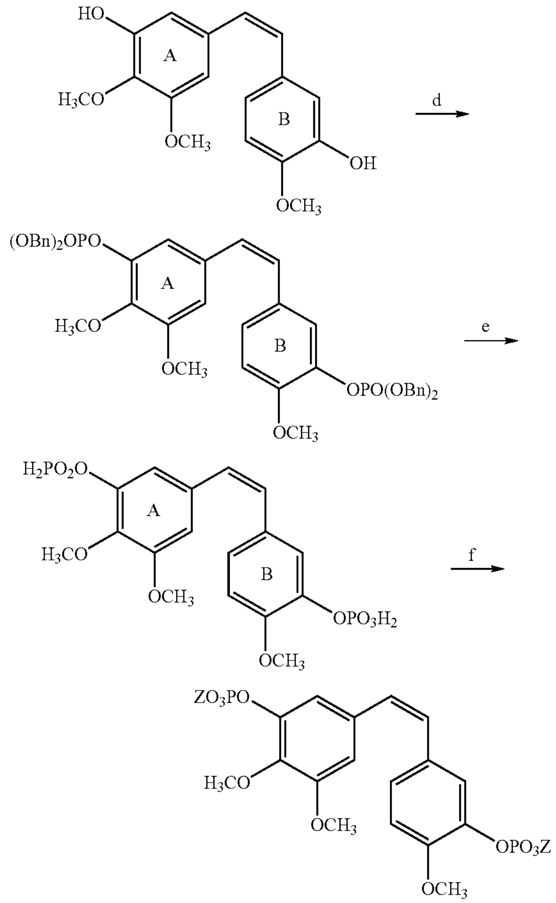

Reagents and Conditions: (a) n-Bu-Li, THF, −78° C.; (b) 4-5-Dimethoxy-3-O-tert-butyldimethyl silyloxy-benzaldehyde in 20 mL THF; (c) 1M TBAF; (d) $CCl_4$, DIPEA, DMAP, Dibenzyl phosphite, −10° C., ACN; (e) TMSBr, $CH_2Cl_2$; (f) sodium methoxide and ethanol.

2. A compound having the following structure:

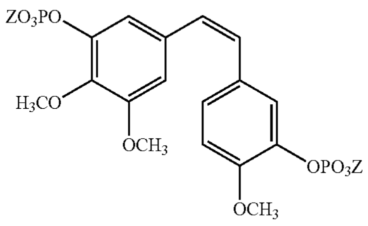

wherein Z is a cation selected from the group consisting of sodium, lithium, potassium, rubidium, calcium, zinc, manganese and magnesium or Z is an amine selected from the group consisting of quinine, quinidine, morpholine and nicotinamide.

3. A method for preparing the compound of claim 2, comprising the steps of:

(a) Phosphorylating combretastatin A-3 with dibenzyl phosphite to provide a phosphate 2b

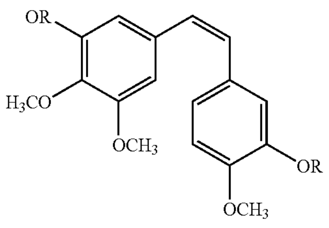

wherein R=PO(OBn)$_2$ (b) debenzylating phosphate ester 2b using bromotrimethylsilane; and (c) adding a base selected from bases containing sodium, lithium, potassium, rubidium, calcium, zinc, manganese, magnesium, quinine, quinidine, morpholine and nicotinamide, to produce said compound.

4. The method of claim 3, wherein Z is sodium and step (c) comprises adding sodium methoxide.

5. A method of treating human and animal subjects afflicted with neoplastic disease selected from the group consisting of leukemia, pancreatic cancer, breast cancer, central nervous system cancer, lung cancer, colon cancer and prostate cancer, comprising administering to said subjects an effective amount of a compound of claim 2 in a pharmacologically acceptable carrier.

6. The method of claim 4, further comprising adding methanol before step (c).

* * * * *